(12) United States Patent
Koyama

(10) Patent No.: US 8,464,577 B2
(45) Date of Patent: Jun. 18, 2013

(54) QUARTZ SENSOR AND SENSING DEVICE

(75) Inventor: Mitsuaki Koyama, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 377 days.

(21) Appl. No.: 12/798,556

(22) Filed: Apr. 7, 2010

(65) Prior Publication Data

US 2010/0263437 A1 Oct. 21, 2010

(30) Foreign Application Priority Data

Apr. 15, 2009 (JP) .................................. 2009-099270

(51) Int. Cl.
*G01N 29/00* (2006.01)

(52) U.S. Cl.
USPC ....... 73/64.53; 73/24.01; 73/31.05; 73/61.75; 73/579; 310/311; 310/365

(58) Field of Classification Search
USPC ................. 73/24.01, 0.03, 0.04, 0.06, 31.05, 73/61.75, 64.53, 579; 310/311, 365
See application file for complete search history.

(56) References Cited

U.S. PATENT DOCUMENTS

| | | | | |
|---|---|---|---|---|
| 5,250,170 | A * | 10/1993 | Yagawara et al. ............. | 204/431 |
| 7,554,247 | B2 * | 6/2009 | Wakamatsu et al. .......... | 310/344 |
| 8,176,773 | B2 * | 5/2012 | Yamakawa et al. .......... | 73/61.49 |
| 2008/0100176 | A1 * | 5/2008 | Haskell et al. ............ | 310/313 R |
| 2008/0129148 | A1 | 6/2008 | Wakamatsu et al. | |
| 2009/0288488 | A1 * | 11/2009 | Yamakawa et al. ............. | 73/579 |
| 2011/0309720 | A1 * | 12/2011 | Kawahara ................ | 310/313 R |

FOREIGN PATENT DOCUMENTS

| | | | |
|---|---|---|---|
| EP | 1 830 170 | | 9/2007 |
| JP | 2004-264254 | * | 3/2004 |
| JP | 2004264254 | * | 3/2004 |
| JP | 2004-264254 | | 9/2004 |
| JP | 2006-029873 | | 2/2006 |
| JP | 2006-033195 | | 2/2006 |
| JP | 2006-078181 | | 3/2006 |

OTHER PUBLICATIONS

Takeru Muto et al: "Examination for realization of a high precision crystal sensor", Frequency Control Symposium, 2008 IEEE International, IEEE, Piscataway, NJ, USA, May 19, 2008, pp. 532-534, CP031319924, ISBN: 978-1-4244-1794-0 *the whole document*.

(Continued)

*Primary Examiner* — Hezron E Williams
*Assistant Examiner* — Hoang Nguyen
(74) *Attorney, Agent, or Firm* — Jordan and Hamburg LLP

(57) ABSTRACT

To provide a quartz sensor capable of detecting a sensing target with high sensitivity also in measurement in a liquid phase in which a difference in Q values at the time of measurement in the liquid phase and in a vapor phase is small. In a quartz sensor 1 including an AT-cut quartz plate 11 having a capture layer (absorbing layer) 12 formed on one surface (XZ' surface) thereof and detecting a sensing target based on an amount of change in a frequency of a quartz resonator 10 caused when the sensing target is absorbed by the capture layer 12, there are formed electrodes 13 for oscillating the quartz plate 11 on end faces (XY' surfaces) mutually opposite in a Z' direction of the surface of the quartz resonator 10 on which the capture layer 12 is formed (XZ' surface).

12 Claims, 25 Drawing Sheets

OTHER PUBLICATIONS

R. Bechmann Parallel Field Excitation of Thickness Modes of Quartz Plates 14th Annual Symposium on Frequency Control 1960, pp. 68-88.

Bechmann R: "Excitation of Piezoelectric Plates by Use of a Parallel Field with Particular Reference to Thickness Modes of Quartz", Proceedings of the IRE, vol. 46, Jul. 1, 1960, pp. 1278-1280.

* cited by examiner

Fig. 2
(a)
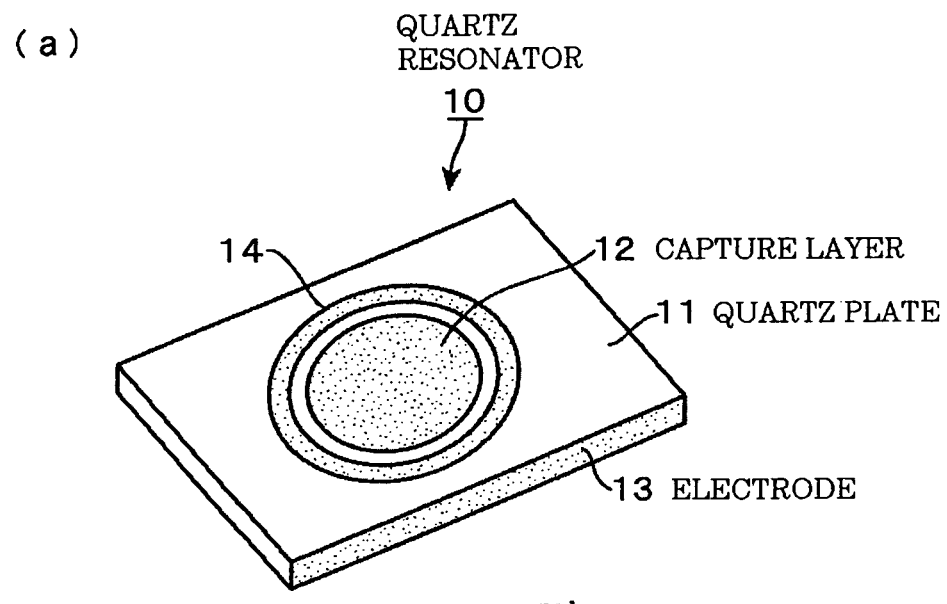
(b)
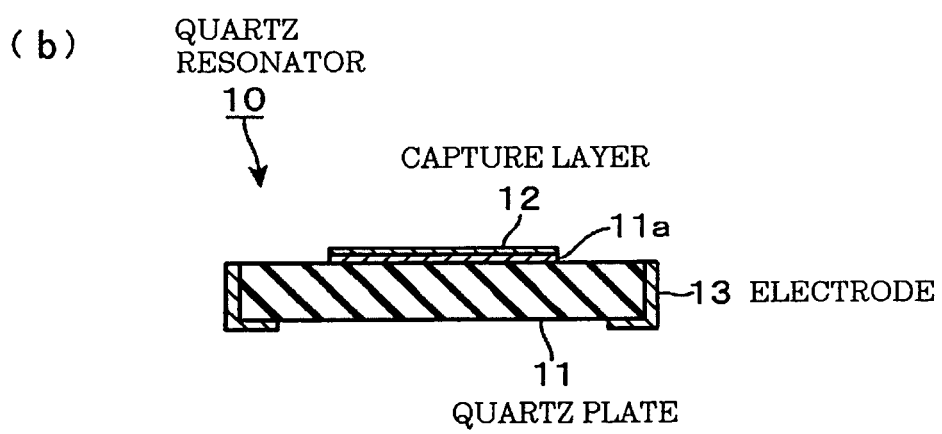

Fig. 4
(a)
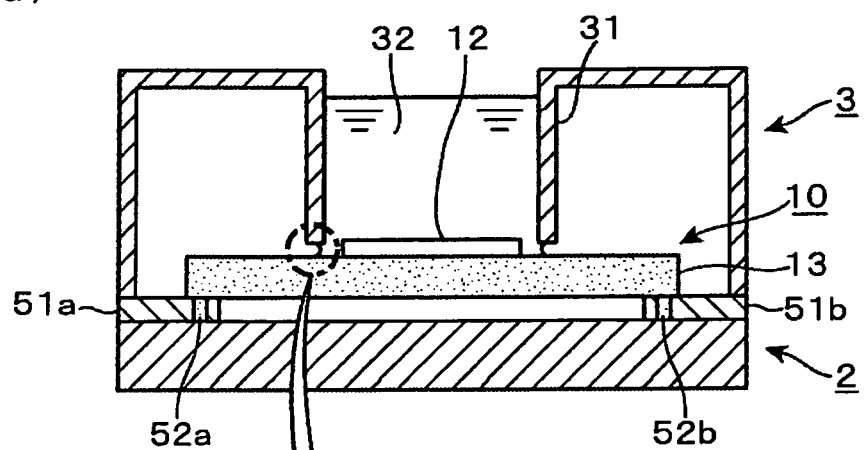
(b)
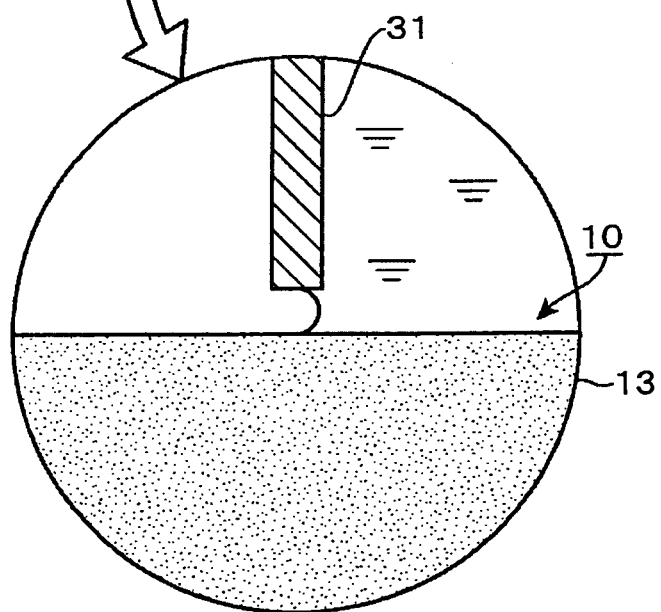

Fig. 17
(a)
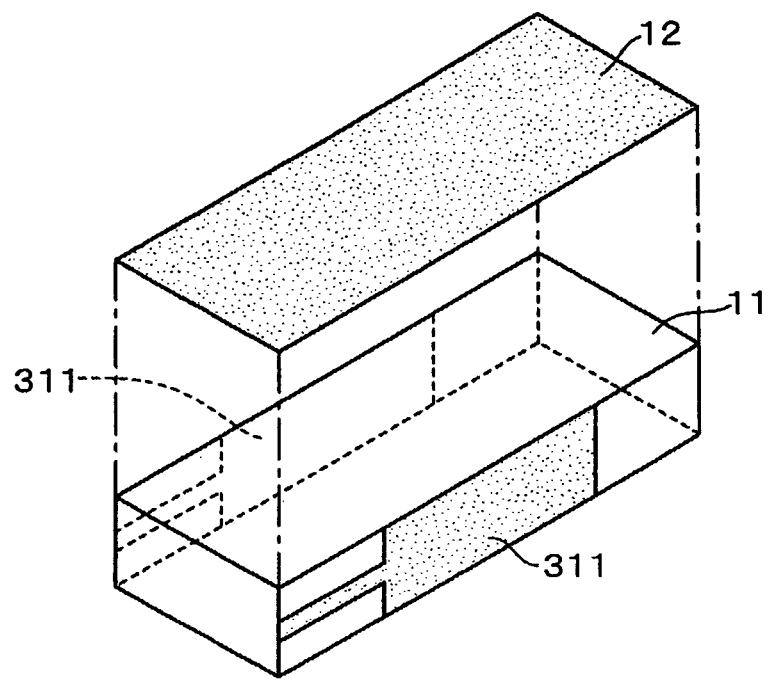
(b)
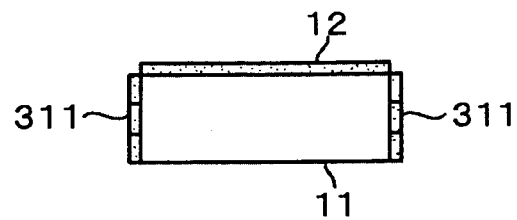

Fig. 18
(a)
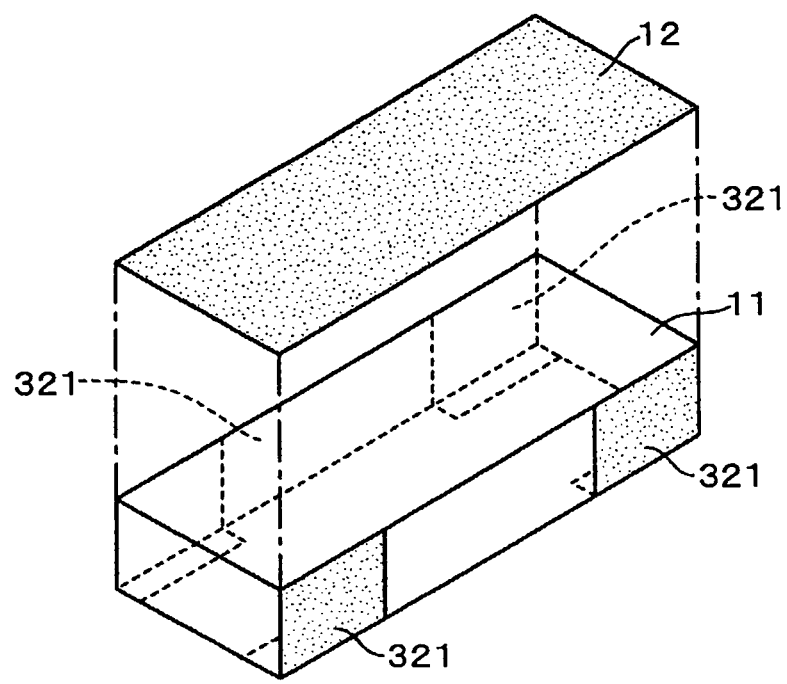
(b)
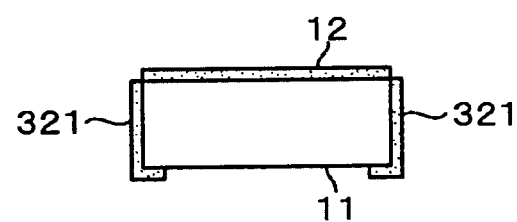

Fig. 19
(a)
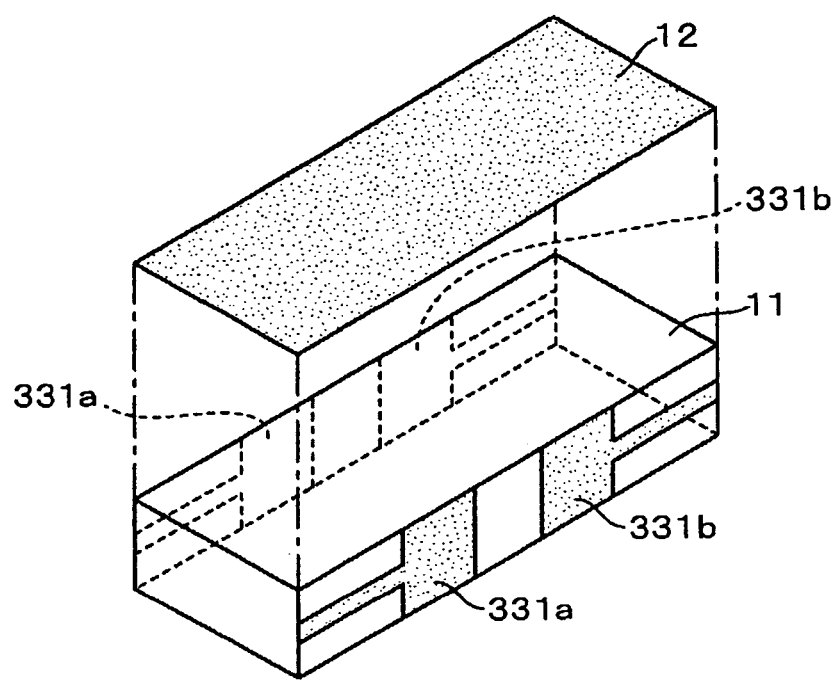
(b)
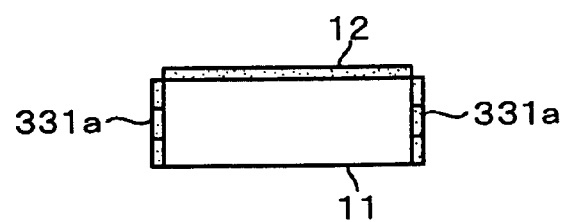

Fig. 20
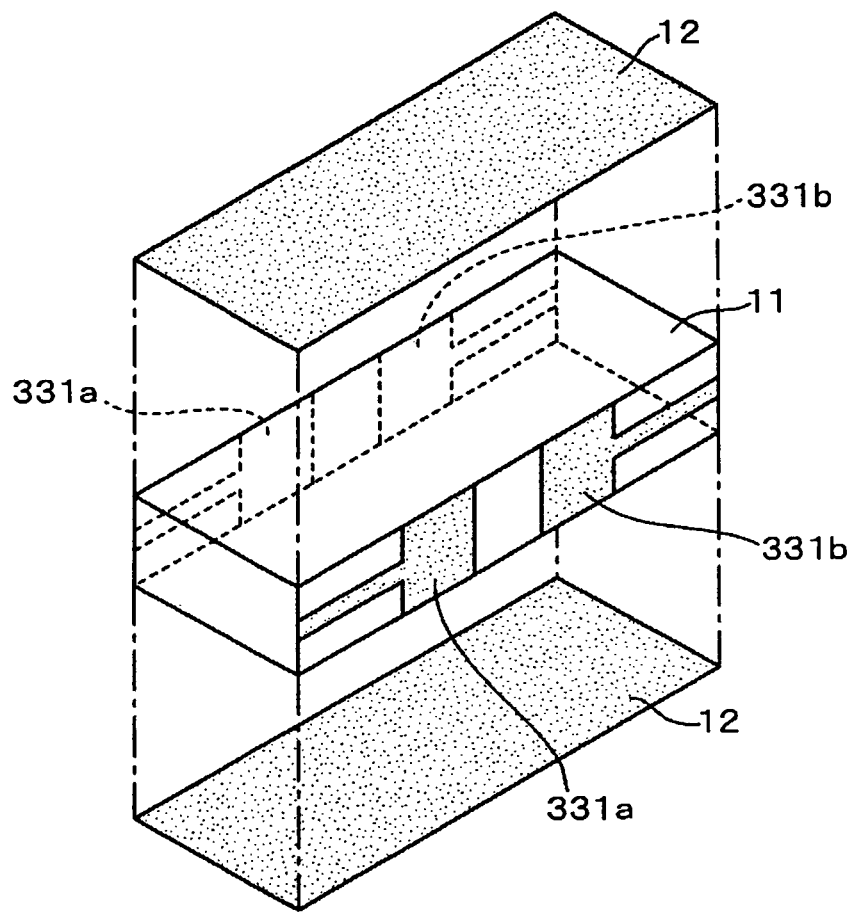
(a)
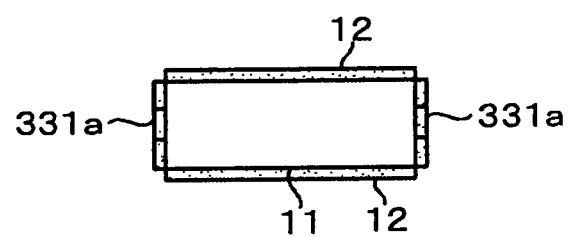
(b)

Fig. 21
(a)
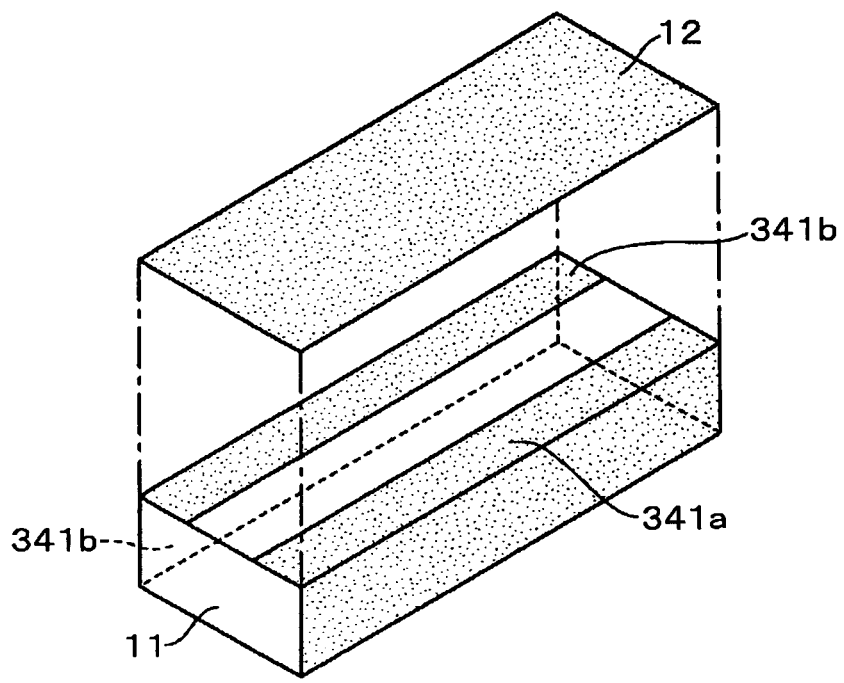
(b)
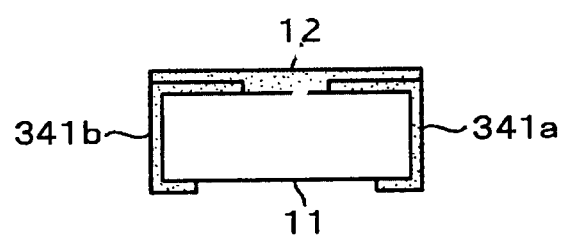

Fig. 22
(a)
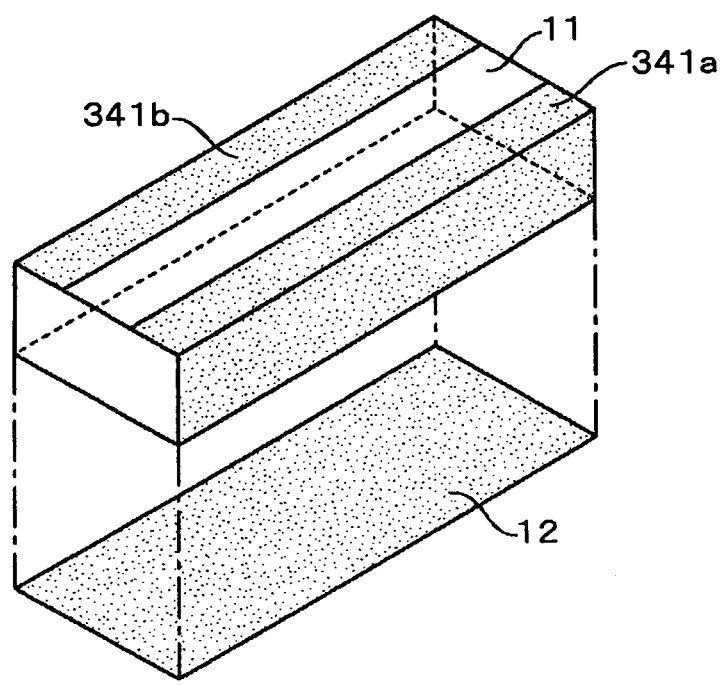
(b)
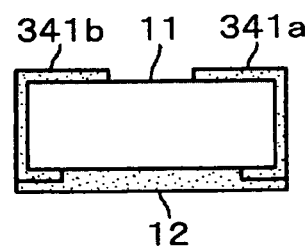

Fig. 23
(a)
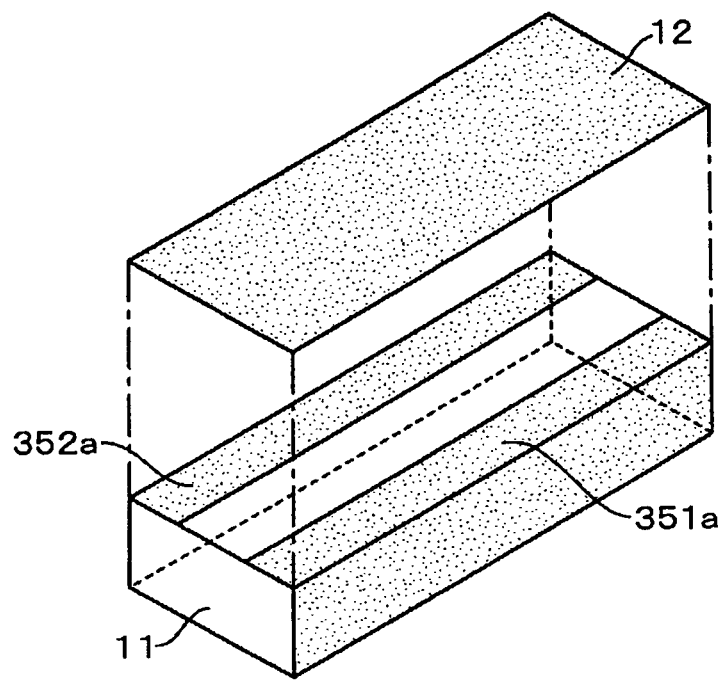
(b)
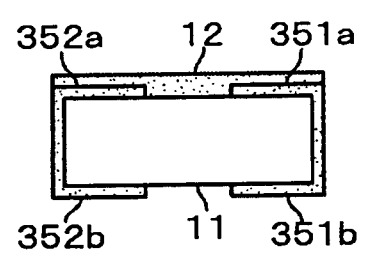

Fig. 24
(a)
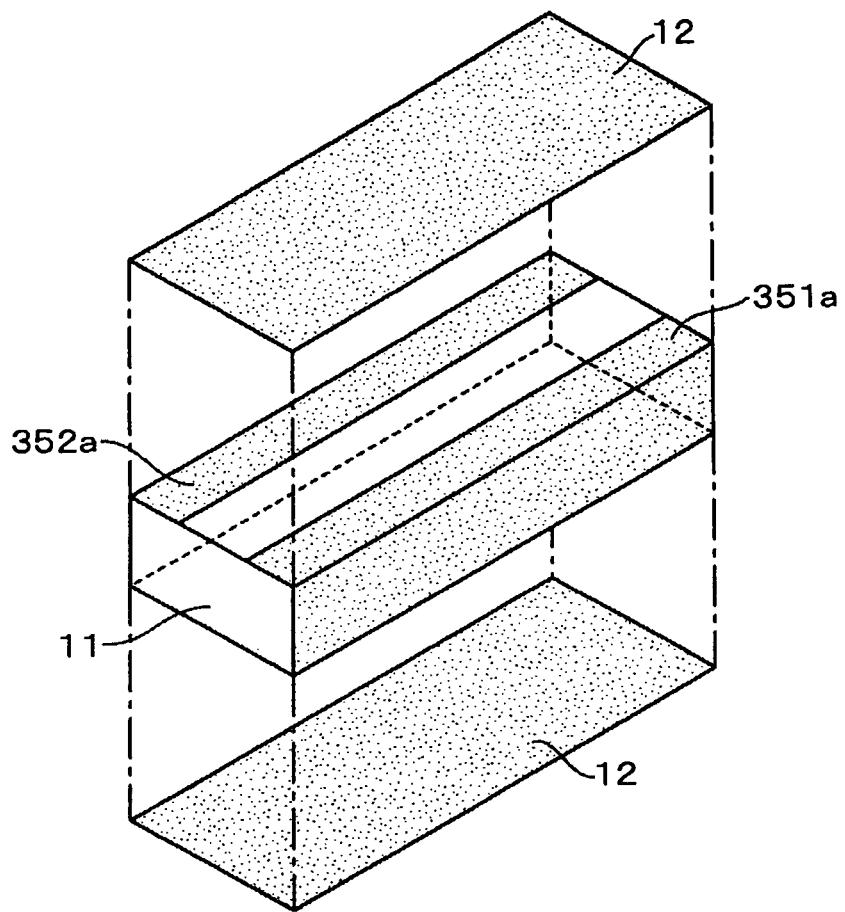
(b)
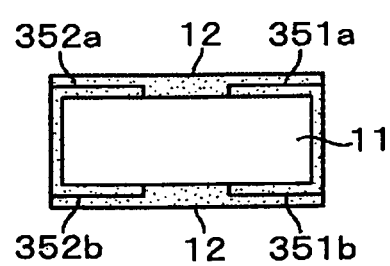

Fig. 25
(a)
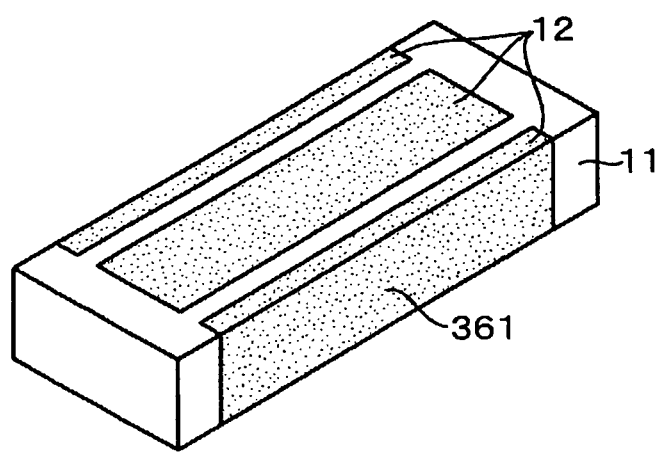
(b)
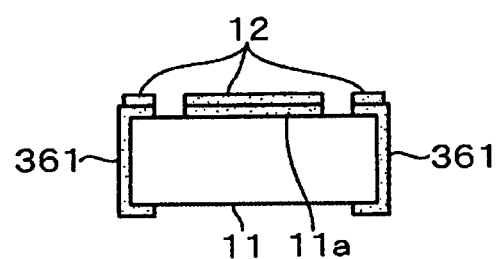

QUARTZ SENSOR AND SENSING DEVICE

BACKGROUND OF THE INVENTION

1. Field of the Invention

The present invention relates to a quartz sensor and a sensing device capable of measuring a sensing target in a liquid phase with high reliability.

2. Description of the Related Art

As a sensing sensor that senses and measures a small amount of substances, there is utilized a quartz sensor that uses, for instance, a quartz resonator. The quartz sensor is a sensor having an absorbing layer formed on a surface of a quartz plate thereof and measuring a concentration of a sensing target by utilizing a characteristic such that when the sensing target adheres to a surface of the absorbing layer, a natural frequency of the crystalline quartz is changed by the amount of weight of the adhered sensing target through a mass addition effect. As the absorbing layer, antibodies such as, for instance, proteins are used, and by utilizing an antibody-antigen reaction, an absorption (capture through reaction) of antigens in sample solution, which is, for instance, blood, is conducted.

As the quartz resonator used in the quartz sensor, there is known a quartz resonator called vertical field excitation type in which electrodes are formed on a front surface and a rear surface of an AT-cut quartz plate, as disclosed in Patent Document 1, for instance, and in this case, an absorbing layer is formed on the electrode on the front surface side. This type of quartz resonator, which is, for instance, a quartz resonator of 9 MHz has a series resistance of an equivalent circuit of about 10Ω, for example, in a vapor phase, but, it has the series resistance of about 200 to 300Ω in a liquid phase, which is, for instance, pure water. In the quartz sensor including the quartz resonator, the series resistance is changed due to a viscosity of the solution and, since the series resistance in the liquid phase is small, the amount of change due to the viscosity becomes large, which affects the change in resonant frequency when an oscillation is applied, resulting in that the reliability of measured results is lowered. In order to prevent the resonant frequency from being affected by the amount of change in the series resistance or to reduce the amount of change to a negligible level, it is only required to structure the quartz sensor so that the series resistance of the quartz resonator takes a large value, which is, for instance, a value of 3 kΩ.

Meanwhile, the quartz resonator of the vertical field excitation type has a Q value ($f_0/\Delta f$: $f_0$ is a resonant frequency, and $\Delta f$ is a frequency band (width of a resonance curve) corresponding to $1/\sqrt{2}$ of a maximum value of a resonant current in the resonance curve) in the liquid phase which is lower than that in the vapor phase, in which the Q value in the atmosphere is about 60000, but, it decreases to about 2000 in the water, for instance. Generally, when the Q value is low, the stability of the quartz resonator is bad and an electronic noise is large. Therefore, it can be said that there exist such problems also when the measurement is conducted in the liquid phase using the quartz resonator, and accordingly, there is desired a technique with which a higher reliability can be secured.

[Patent Document 1] Japanese Patent Application Laid-open No. 2006-78181

SUMMARY OF THE INVENTION

The present invention has been made based on such circumstances, and an object thereof is to provide a quartz sensor and a sensing device capable obtaining a high reliability at the time of measuring a sensing target in sample solution.

A quartz sensor of the present invention having a capture layer for capturing a sensing target in sample solution formed on a plate surface of an AT-cut quartz plate thereof and sensing the sensing target based on a change in a natural frequency of the quartz plate caused when the sensing target is captured by the capture layer, the quartz sensor is characterized by including electrodes for vibrating the quartz plate provided on mutually opposite end faces of the quartz plate.

Further, the quartz sensor may take structures as follows.

1. A structure in which a metal layer insulated from the electrodes is formed on the plate surface of the quartz plate, and the capture layer is formed on the metal layer.

2. A structure in which, when the electrodes provided on the end faces of the quartz plate are set as first electrodes, there are mutually opposite second electrodes each provided on a part of each of both plate surfaces of the quartz plate, and the first electrodes and the second electrodes are electrically connected to one another.

3. A structure in which the first electrodes and the second electrodes are electrically connected to one another on the quartz plate.

A sensing device according to the present invention is characterized by including: the quartz sensor; an oscillation circuit connected to the quartz sensor; and a measuring section measuring a frequency signal from the oscillation circuit.

According to the present invention, a balanced field excitation type quartz resonator is structured in a quartz sensor using an AT-cut quartz plate by providing a capture layer on a plate surface of the quartz plate and providing electrodes on end faces mutually opposite in a Z' direction of the plate surface, so that a high Q value can be obtained also in a liquid phase. Accordingly, the stability of frequency is high, and measurement of sensing target in sample solution can be conducted with high reliability.

BRIEF DESCRIPTION OF THE DRAWINGS

FIGS. 2(a) and 2(b) are a perspective view and a sectional view showing a quartz resonator incorporated in the quartz sensor according to the embodiment of the present invention;

FIGS. 4(a) and 4(b) are a longitudinal sectional view and an enlarged view showing the quartz sensor;

FIGS. 17(a) and 17(b) are a perspective view and a side view showing a quartz plate according to an another embodiment;

FIGS. 18(a) and 18(b) are a perspective view and a side view showing a quartz plate according to an another embodiment;

FIGS. 19(a) and 19(b) are a perspective view and a side view showing a quartz plate according to an another embodiment;

FIGS. 20(a) and 20(b) are a perspective view and a side view showing a quartz plate according to an another embodiment;

FIGS. 21(a) and 21(b) are a perspective view and a side view showing a quartz plate according to an another embodiment;

FIGS. 22(a) and 22(b) are a perspective view and a side view showing a quartz plate according to an another embodiment;

FIGS. 23(a) and 23(b) are a perspective view and a side view showing a quartz plate according to an another embodiment;

FIGS. 24(a) and 24(b) are a perspective view and a side view showing a quartz plate according to an another embodiment; and FIGS. 25(a) and 25(b) are a perspective view and a side view showing a quartz plate according to an another embodiment.

DETAILED DESCRIPTION OF THE PREFERRED EMBODIMENT(S)

Figure 1:
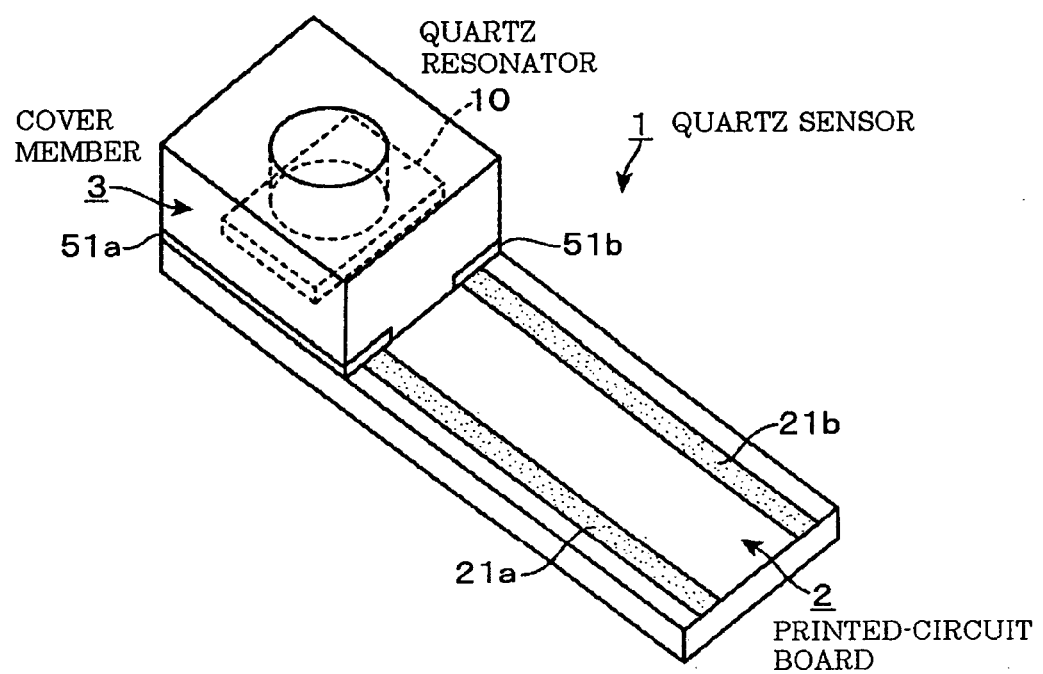
FIG. 1 is a perspective view showing a quartz sensor according to an embodiment of the present invention.

A quartz sensor according to an embodiment of the present invention will be described. As shown in FIG. 1, a quartz sensor 1 includes a quartz resonator 10, a printed-circuit board 2, and a cover member 3. As shown in FIG. 2, the quartz resonator 10 is, for instance, an AT-cut strip-shaped quartz plate 11 having a long edge extending along an X axis of the crystalline quartz, and a short edge extending along a Z' axis (an axis corresponding to a Z axis that is inclined by 35° 15') of the crystalline quartz, and whose thickness direction corresponds to a Y' axis (an axis corresponding to a Y axis that is inclined by 35° 15') of the crystalline quartz. On one plate surface of the quartz plate 11 of the quartz resonator 10 (upper surface: XZ' surface in FIG. 2(a)), a metal layer 11a (refer to FIG. 2(b)) is formed in a circular shape, and on a surface of the metal layer 11a, there is formed a capture layer (absorbing layer) 12 for capturing, for instance, an antigen being a sensing target through an antigen-antibody reaction. The metal layer 11a is formed by, for example, laminating gold on chromium (Cr) being an adhesive layer. Electrodes 13 for oscillating the quartz plate 11 are formed on end faces mutually opposite in a Z' direction of the quartz plate 11, and lower end portions of the electrodes 13 extend to the other surface side of the quartz plate 11 (lower surface side in FIG. 2(a)) so that the electrodes can be connected to later-described conductive paths of printed-circuit board. The metal layer 11a and the electrodes 13 are simultaneously formed through, for example, photolithography. Further, on an outer edge area of the capture layer 12 on the quartz plate 11 and a portion facing to a lower end portion of a later-described cylindrical body of cover member, a water repellent layer 14 is formed in a ring shape. The water repellent layer 14 is for preventing sample solution from flowing out from a space between the lower end portion of the cylindrical body and the surface of the quartz resonator 10.

Figure 3:
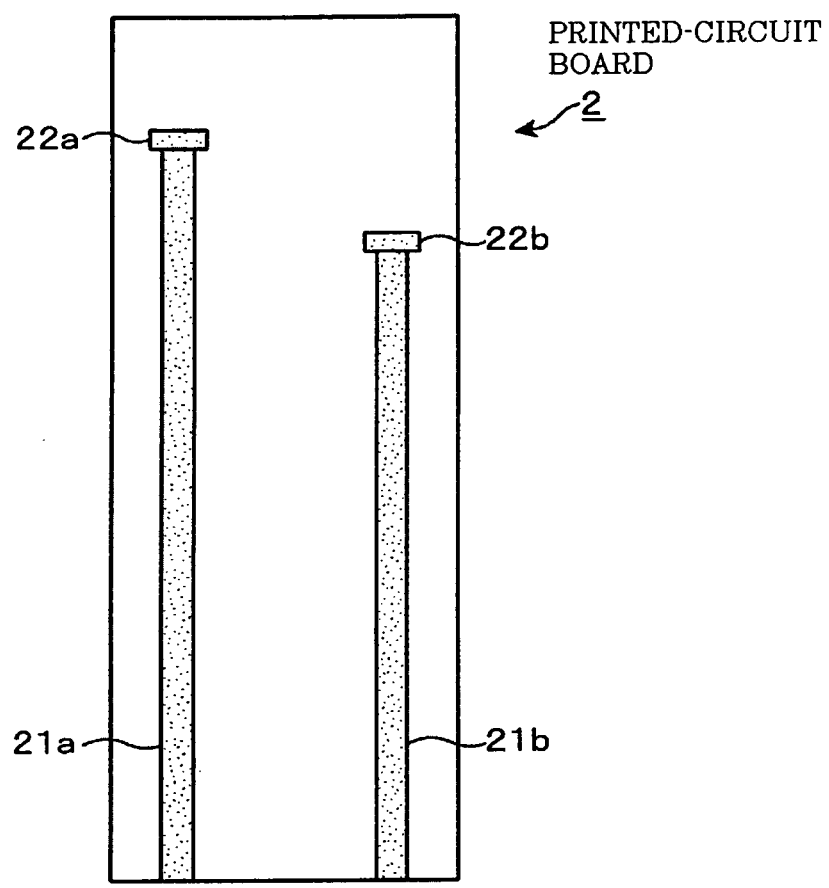
FIG. 3 is a top view of a printed-circuit board that forms a part of the quartz sensor.

As shown in FIG. 3, conductive paths 21a, 21b are provided in parallel on the printed-circuit board 2 from one end side toward the other end side of the surface of the board. Further, one end sides of the conductive paths 21a, 21b are formed as electrodes 22a, 22b to be connected to later-described electrodes on a side of spacers, and the other end sides of the conductive paths 21a, 21b serve as connecting terminals to be connected to later-described connecting terminal portions of oscillation circuit.

As shown in FIG. 1 and FIG. 4(a), a square box-shaped cover member 3 is provided to cover one end side area of the printed-circuit board 2. Here, if both edges extending in a longitudinal direction of the printed-circuit board 2 are respectively called as a left edge and a right edge, three edges of the cover member 3 are respectively formed along one end edge, the left edge, and the right edge of the printed-circuit board 2. Between the cover member 3 and the printed-circuit board 2, strip-shaped spacers 51a, 51b formed of, for instance, resins, rubbers or the like, and extending along the left edge and the right edge, respectively, are interposed. The quartz resonator 10 is disposed to stride over the spacers 51a, 51b so that edge portions thereof mutually opposite in an X direction and on which no electrodes are provided become parallel to the left edge (right edge) of the printed-circuit board 2, and contact positions of the quartz resonator 10 and the spacers 51a, 51b are outside a later-described solution storage space of sample solution.

On both upper and lower surfaces of the spacers 51a, 51b, electrodes (not shown) are formed, and to mutually connect these electrodes, conductive paths 52a, 52b are provided in a thickness direction of the spacers 51a, 51b, as shown in FIG. 4(a). The electrodes on the upper surface side of the spacers 51a, 51b contact with the electrodes 13 on the lower surface side of the quartz resonator 10 (refer to FIG. 2(b)), and the electrodes on the lower surface side of the spacers 51a, 51b respectively contact with the end portions (electrodes) 22a, 22b of the conductive paths 21a, 21b of the printed-circuit board 2. Accordingly, when a voltage is applied to the conductive paths 21a, 21b of the printed-circuit board 2, the voltage is applied to the electrodes 13 of the quartz resonator 10.

Figure 5:
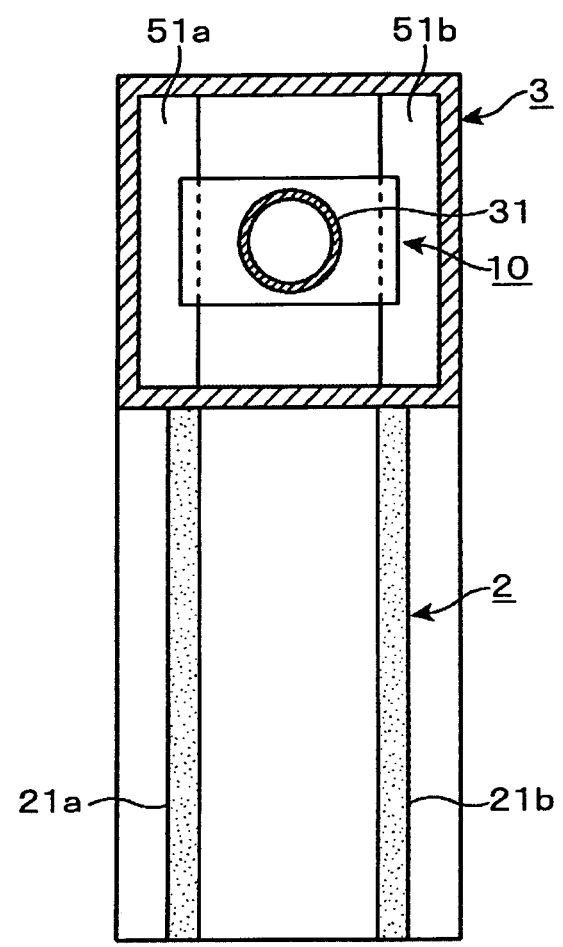
FIG. 5 is a top view showing the quartz sensor.

As shown in FIG. 4 and FIG. 5, a center portion of the cover member 3 is opened, and a cylindrical body 31 extends downward from an opening edge. A lower edge of the cylindrical body 31 is formed to position slightly above the surface of the quartz resonator 10. An area surrounded by the cylindrical body 31 and the surface of the quartz resonator 10 forms a solution storage space 32 for storing sample solution. Further, the cylindrical body 31 is formed of a water repellent member which repels the sample solution together with the aforementioned water repellent layer 14 formed on the surface of the quartz plate 11, and with the use of a surface tension thereof, the sample solution is prevented from being leaked to the outside from the solution storage space 32 via a space between the lower edge of the cylindrical body 31 and the surface of the quartz resonator 10 (refer to FIG. 4(b)).

Figure 6:
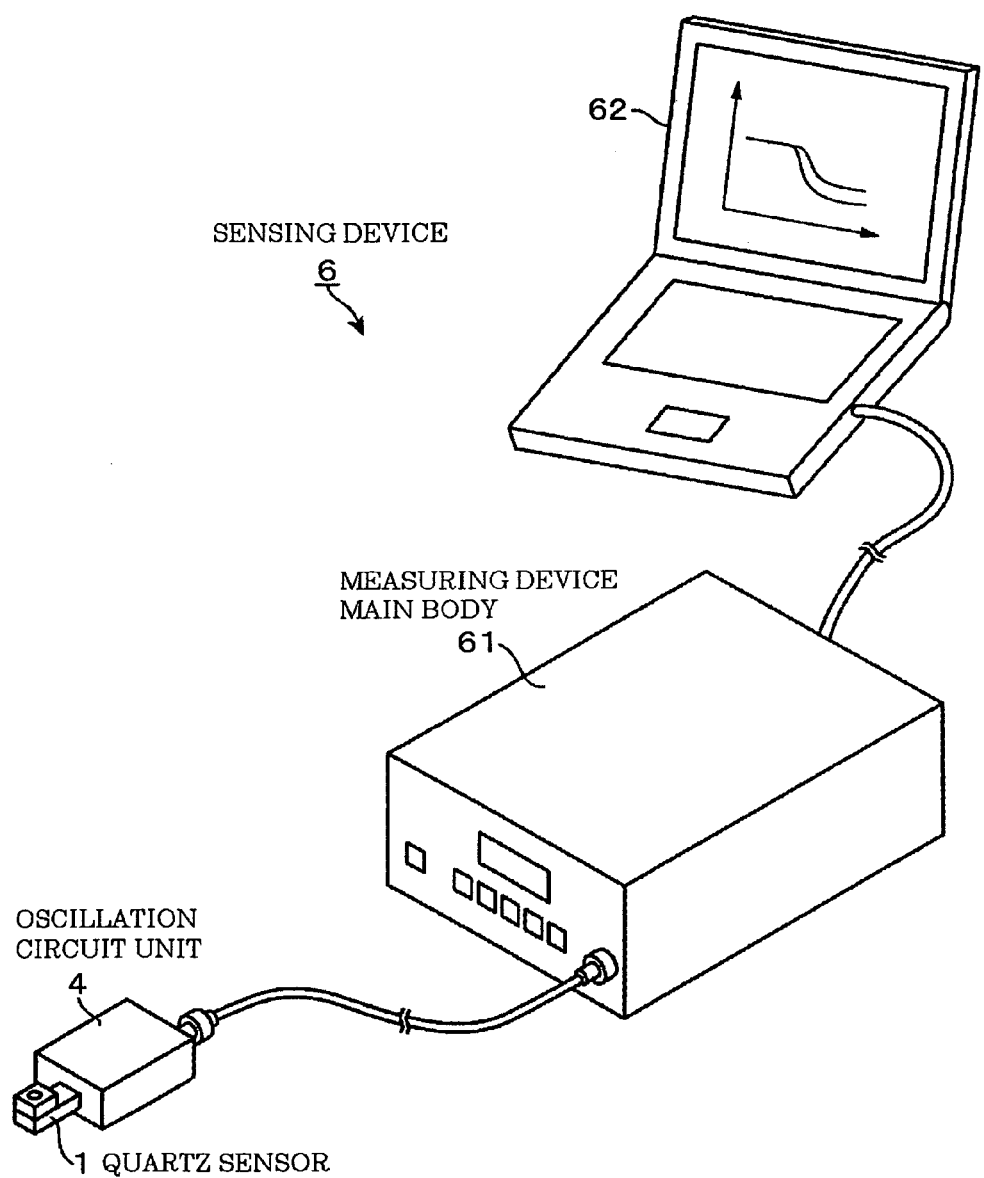
FIG. 6 is a perspective view showing a sensing device according to the present invention.
Figure 8:
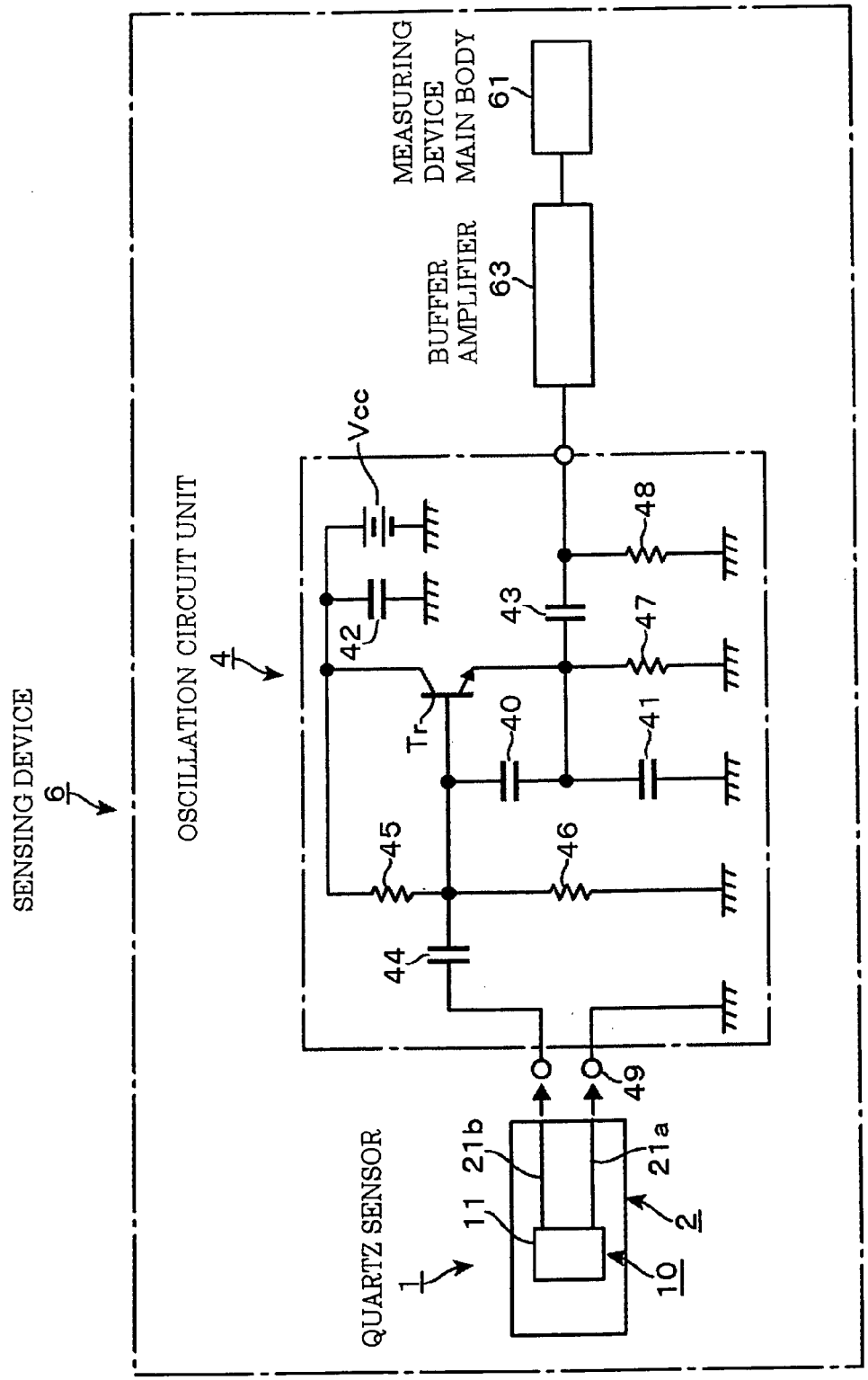
FIG. 8 is a block diagram showing the sensing device.

Next, a sensing device 6 will be described. As shown in FIG. 6, the sensing device 6 includes the quartz sensor 1, an oscillation circuit unit 4 including an oscillation circuit to which the quartz sensor 1 is detachably attached, and a measuring section including a measuring device main body 61 and, for instance, a personal computer 62. The terminal portions (conductive paths) 21a, 21b of the printed-circuit board 2 of the quartz sensor 1 are connected to terminal portions 49 of the oscillation circuit unit 4, and the oscillation circuit unit 4 is electrically connected to the measuring device main body 61 via a coaxial cable, for instance. The oscillation circuit in the oscillation circuit unit 4 is formed as a Colpitts-type oscillation circuit unit, and serves to oscillate the quartz resonator 10 of the quartz sensor 1. In FIG. 8, Tr denotes a transistor as an oscillation amplifying element, 40, 41 denote capacitors forming divided capacitive components, and Vcc denotes a constant voltage source. As for other portions, 42 to 44 denote capacitors, and 45 to 48 denote resistors. On a subsequent stage of the oscillation circuit unit 4, the measuring device main body 61 is connected via a buffer amplifier 63. The measuring device main body 61 has a function to measure a signal regarding a frequency of oscillation output of the oscillation circuit unit 4. A frequency counter may be used as a measuring method of the frequency, and it is also possible to adopt a method in which quadrature detection is performed on a frequency signal to calculate a rotating vector that rotates at a frequency being a difference between a frequency of the frequency signal and a frequency of the frequency signal on which the detection is performed, and a change in a phase of the rotating vector is evaluated as a velocity of the rotating vector to determine the velocity.

Figure 7:
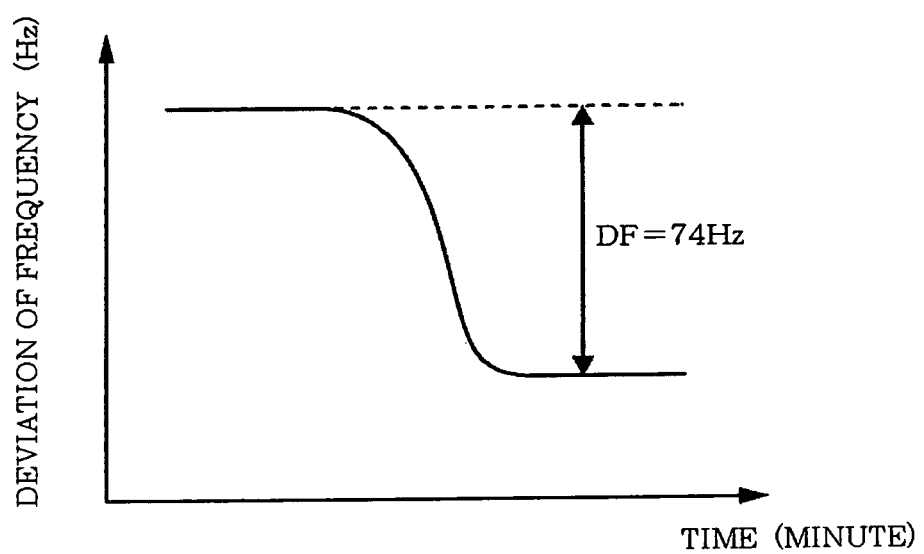
FIG. 7 shows an example of measured results obtained through measurement conducted by using the quartz sensor.

Next, process steps to measure a concentration of sensing target, which is, for instance, a certain type of antigen in blood or serum by using the quartz sensor 1 and the sensing device 6 structured as above, will be described. First, the quartz sensor 1 is inserted into an insertion port of the oscillation circuit unit 4 of the sensing device 6, and through this insertion, the terminal portions (conductive paths) 21a, 21b of the printed-circuit board 2 and the terminal portions 49 of the oscillation circuit unit 4 are electrically connected. Further, the quartz resonator 10 is oscillated by the oscillation circuit unit 4, and the oscillated frequency signal is taken into a measuring section main body 61. Further, when a measuring person injects, for instance, saline solution as diluted solution from the opening portion of the cover member 3 of the quartz sensor 1, the solution storage space 32 is filled with the saline solution, resulting in that an atmosphere of the quartz resonator 10 is changed from the vapor phase to the liquid phase, and a frequency at this time is measured. Subsequently, when sample solution formed of serum as it is or serum diluted by, for example, saline solution, is injected in the solution storage space 32 of the quartz sensor 1 from the opening portion, an antigen contained in the sample solution is captured by an antibody of the absorbing layer through an antigen-antibody reaction. The antigen-antibody reaction progresses, and the value of the frequency is lowered by the mass addition effect. Further, with the use of, for instance, the personal computer 62 connected to the measuring device main body 61, the amount of change in frequency of, for instance, 74 Hz, is determined as shown in FIG. 7, and a concentration of the sensing target is detected based on, for instance, a predetermined formed calibration curve.

Figure 9:
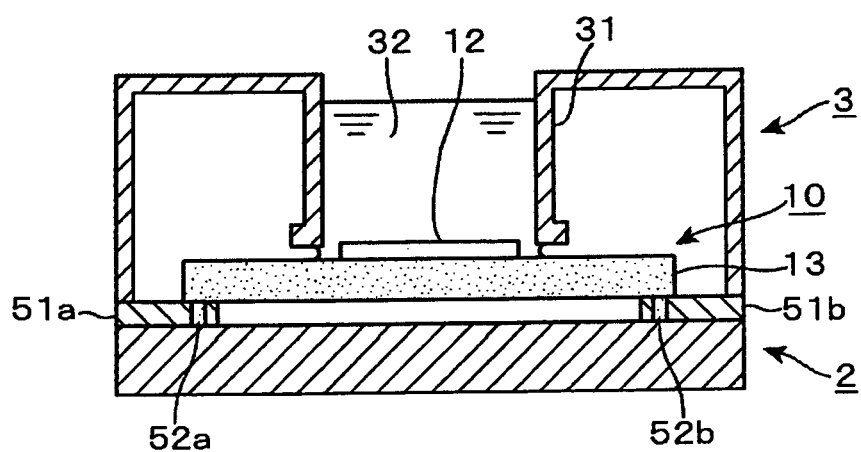
FIG. 9 is a longitudinal sectional view showing a quartz sensor according to an another embodiment.

In the above description, it is also possible that the lower end portion of the cylindrical body 31 of the cover member 3 is formed in a flange shape by being bent to the lateral side, as shown in FIG. 9.

Figure 10:
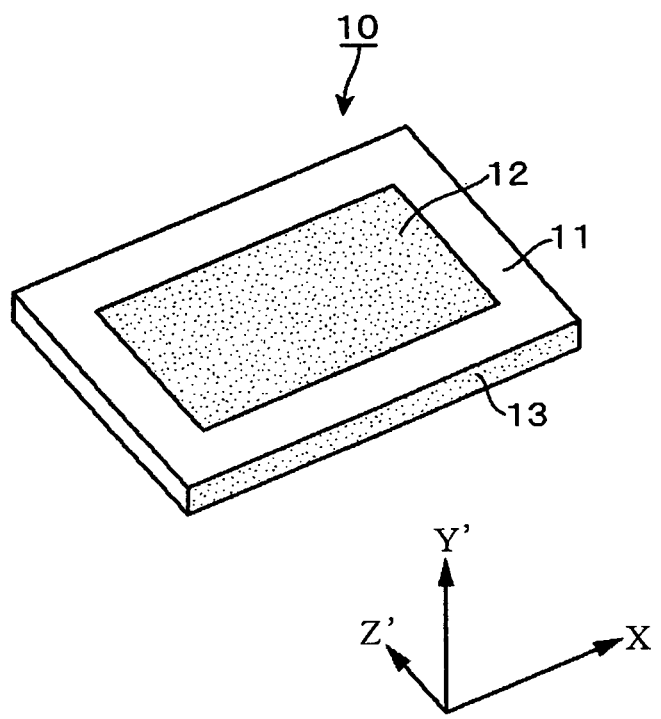
FIG. 10 is a perspective view showing a quartz plate according to an another embodiment.
Figure 11:
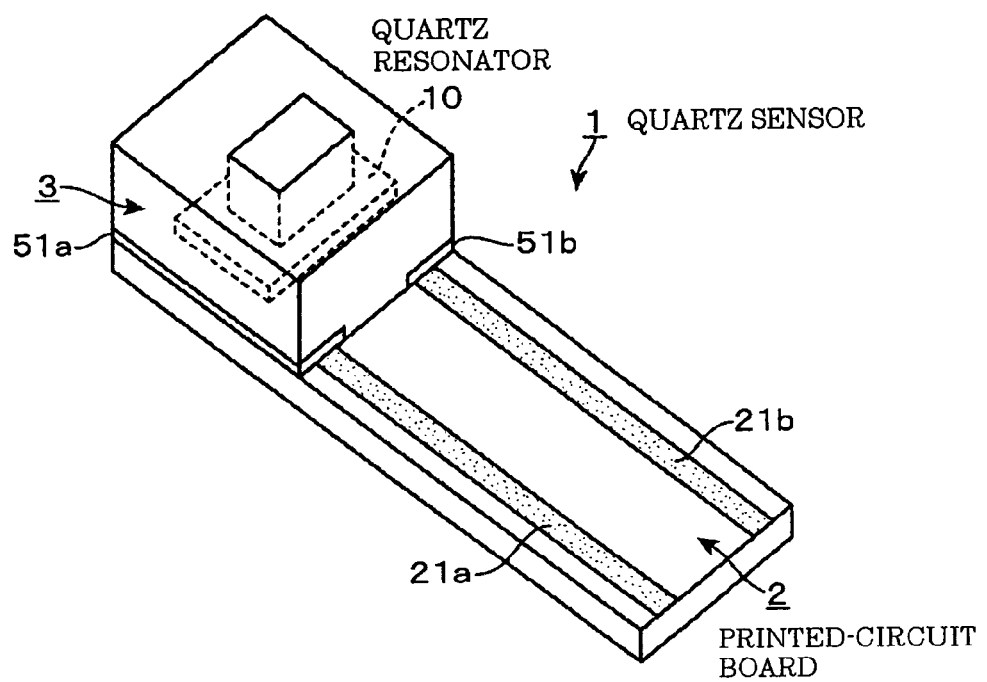
FIG. 11 is a perspective view showing a quartz sensor according to the another embodiment.

Further, it is also possible that the metal layer 11a is formed in a rectangular shape, and the capture layer 12 is formed on the metal layer, as shown in FIG. 10. In this case, the opening portion of the cover member 3 is opened in a rectangular shape to match with the shape of the capture layer 12, and a square-shaped barrel body 31 is provided to extend from the opening edge, as shown in FIG. 11.

According to the aforementioned embodiments, the balanced field excitation type quartz resonator 10 is structured in the quartz sensor 1 using the AT-cut quartz plate 11 by providing the capture layer 12 on the plate surface of the quartz plate 11 and providing the electrodes 13 on the end faces mutually opposite in the Z' direction of the plate surface, so that a high Q value can be obtained also in the liquid phase. Accordingly, the stability of frequency is high, and measurement of sensing target can be conducted with high reliability.

Figure 12:
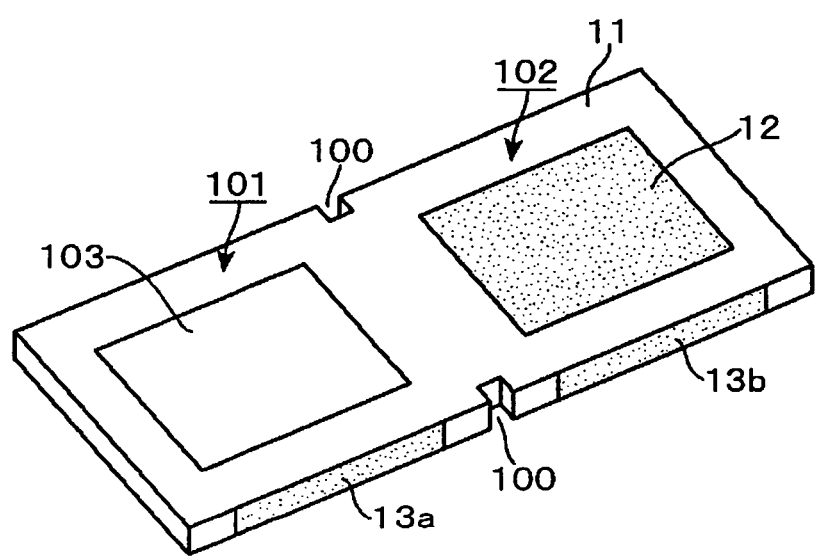
FIG. 12 is a perspective view showing a quartz plate according to an another embodiment.
Figure 13:
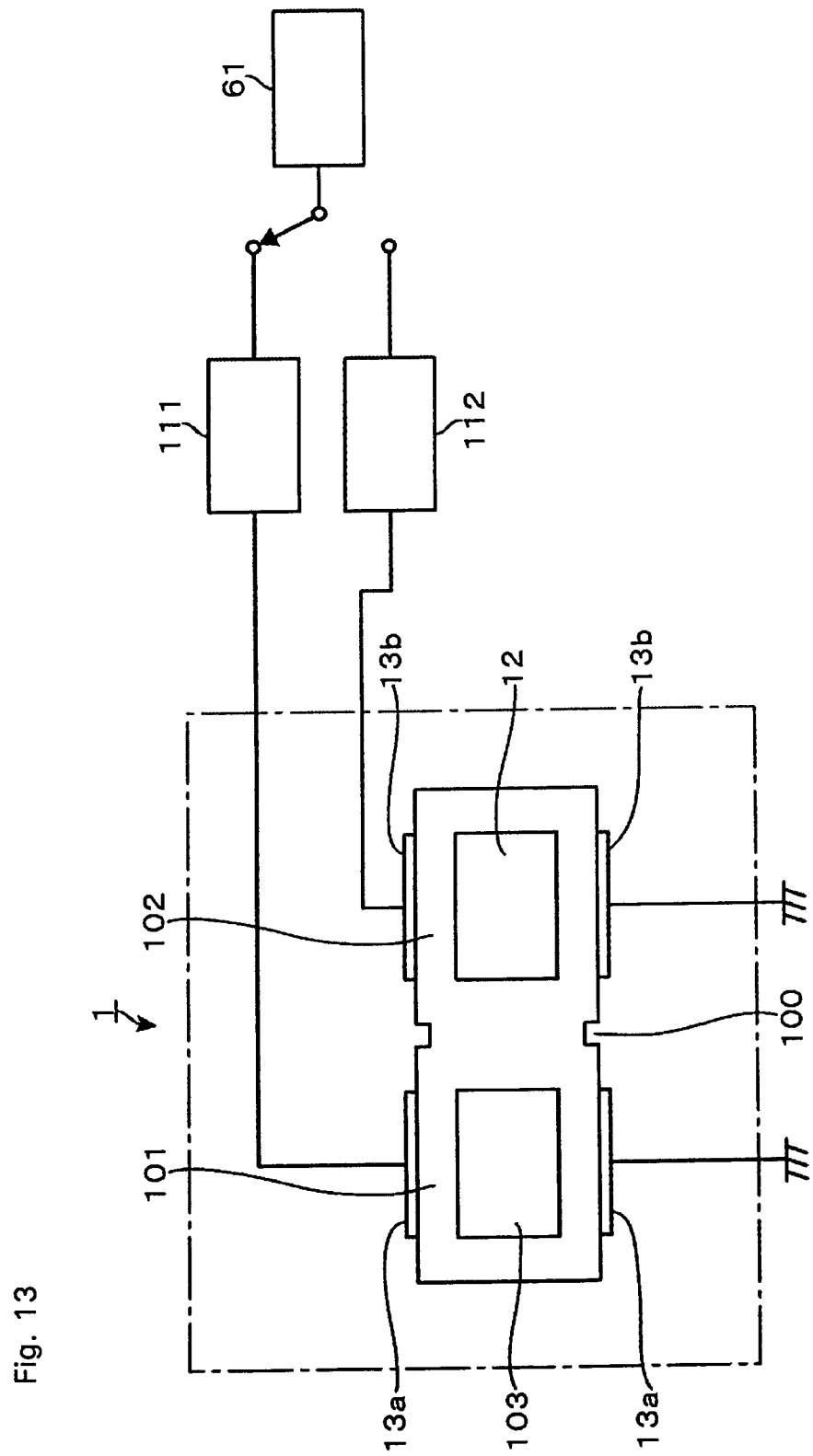
FIG. 13 is a block diagram showing a part of a sensing device according to the another embodiment.

Next, a quartz sensor according to an another embodiment of the present invention will be described. As shown in FIG. 12, on center portions of end faces of the quartz plate 11 used in the quartz sensor 1, there are formed groove portions 100 forming elastic boundary layers, and by the groove portions 100, the quartz plate 11 is divided into two, which are, a first vibration area (left-side area) 101 and a second vibration area (right-side area) 102. On a plate surface of the quartz plate 11 in the first vibration area 101, there is formed a block layer 103 formed of antibodies which do not react with a sensing target via a metal layer, and electrodes 13a are formed on respective end faces of the quartz plate. On a plate surface of the quartz plate 11 in the second vibration area 102, the metal layer 11a is laminated and the capture layer 12 is formed on the metal layer, and electrodes 13b are formed on respective end faces of the quartz plate. Further, the electrodes 13a, 13b are extended to the other surface side (lower surface side) of the quartz plate 11.

Further, when the quartz sensor 1 is inserted into the oscillation circuit unit 4, one electrode 13a on the first vibration area 101 side is connected to an oscillation circuit 111, and the other electrode 13a is grounded, and further, one electrode 13b on the second vibration area 102 side is connected to an oscillation circuit 112, and the other electrode 13b is grounded.

Figure 14:
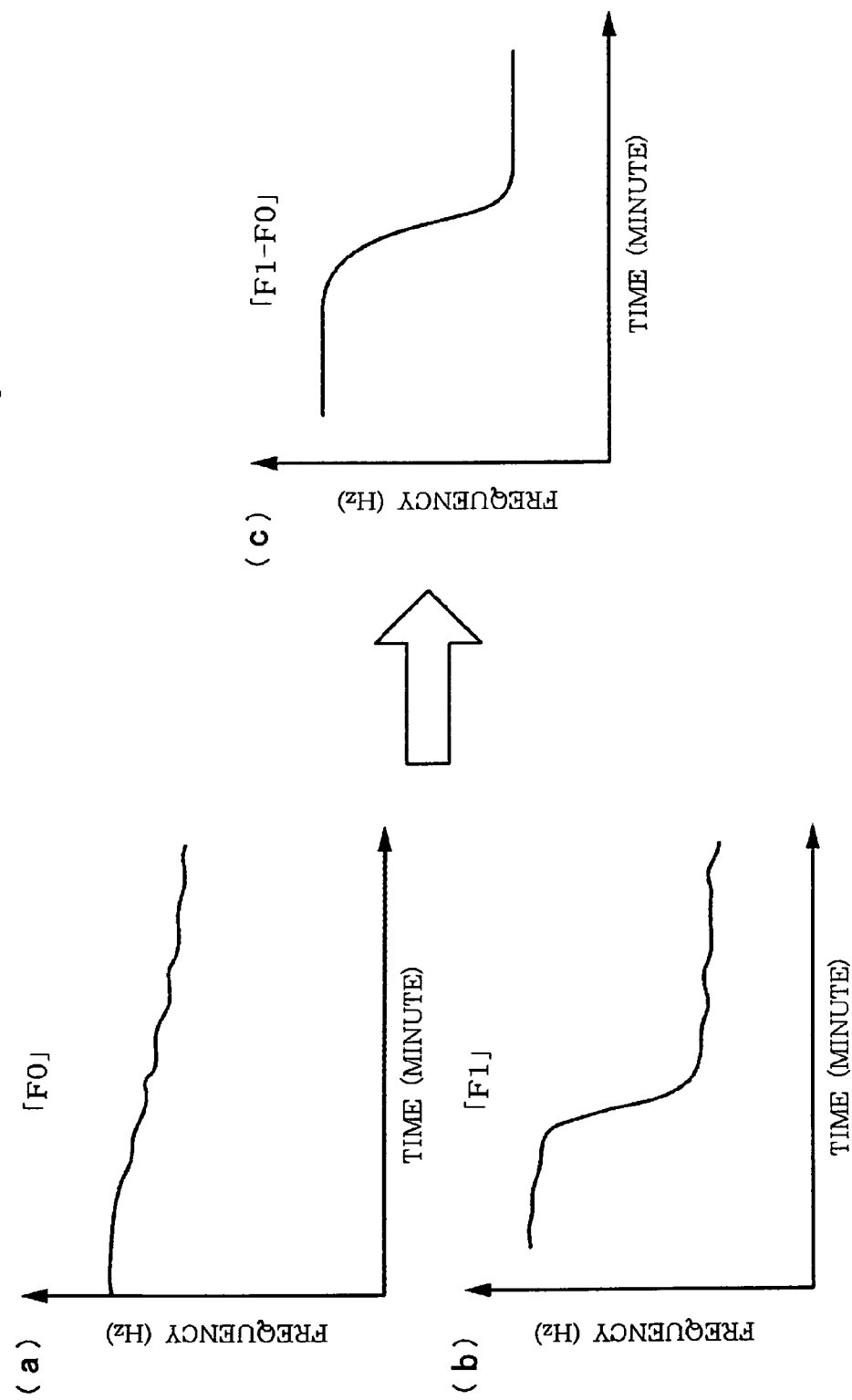
FIGS. 14(a), 14(b) and 14(c) are explanatory diagrams explaining an example of measured results of the sensing device.

In such a quartz sensor 1, since the first vibration area is not affected by a change caused by an absorption of the sensing target, an oscillation frequency "F0" that is changed only by a temperature irrespective of a concentration of the sample solution can be measured (FIG. 14(a)), and in the second vibration area, it is possible to measure an oscillation frequency "F1" that is changed by the concentration of the sample solution changed by the absorption of the sensing target, and the temperature (FIG. 14(b)). Further, even when the temperature is changed around the quartz plate 11, the oscillation frequencies "F0" and "F1" are affected by the temperature change under the same condition. Therefore, by calculating a difference in the oscillation frequencies "F1−F0", it is possible to obtain a highly reliable measured result obtained by removing the frequency change caused by the temperature change (FIG. 14(c)).

Figure 15:
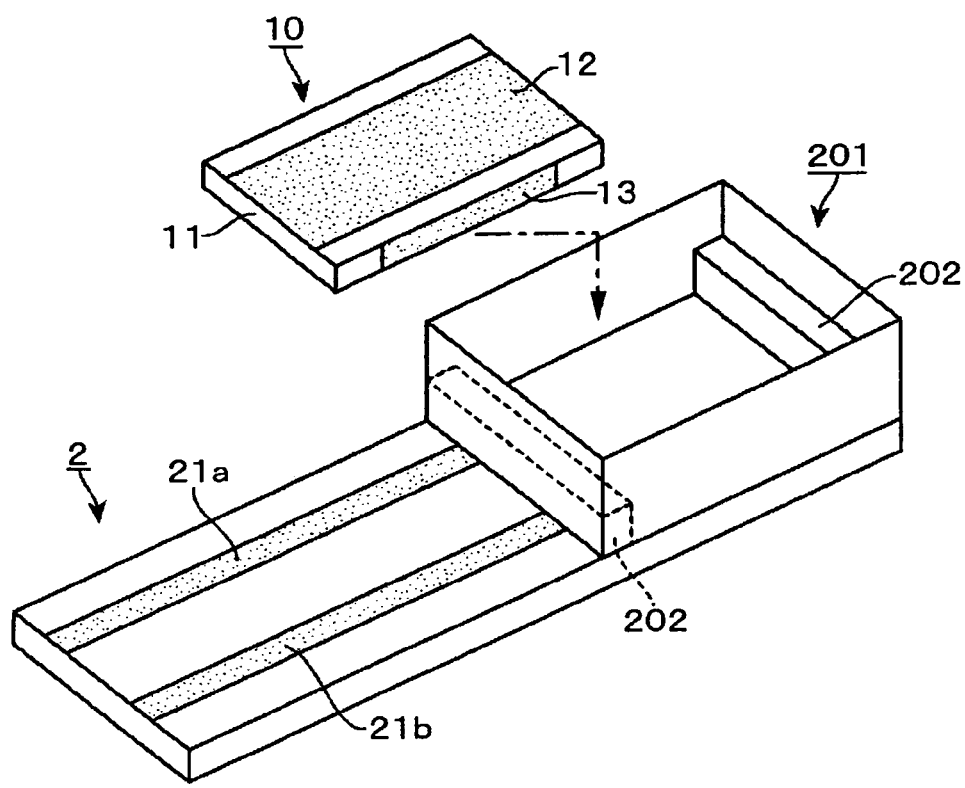
FIG. 15 is a perspective view showing a quartz plate and a quartz sensor according an another embodiment.
Figure 16:
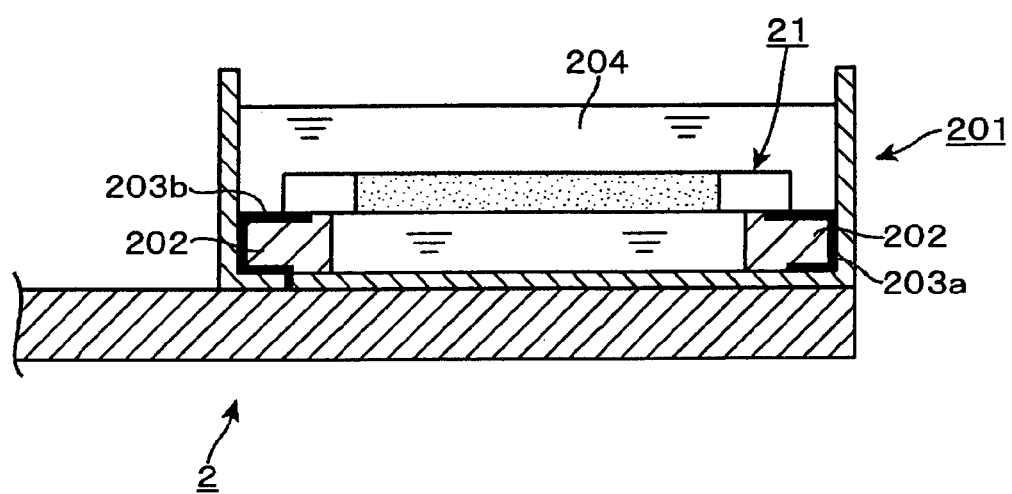
FIG. 16 is a longitudinal sectional view showing the quartz sensor according to the another embodiment.

Further, in a quartz sensor according to an another embodiment of the present invention, a casing 201 whose upper portion is opened is provided on one end side area of the printed-circuit board 2, as shown in FIG. 15. On both end portions inside the casing 201, there are respectively provided mounting members 202 extending in a width direction of the printed-circuit board 2 for mounting the quartz plate 11. The quartz resonator 10 is mounted on the mounting members 202 so that the end faces thereof on which the electrodes 13 are formed position orthogonal to the mounting members 202, and is fixed by, for example, a conductive adhesive. The capture layer 12 of the quartz resonator 10 is formed on a surface of a metal layer separated (insulated) from the electrodes 13 on the end faces of the quartz plate 11, similar to the aforementioned embodiments. Further, conductive paths 203a, 203b are formed on surfaces of the mounting members 202 as shown in FIG. 16, so that when the quartz plate 11 is mounted on the mounting members 202, the electrodes 13 extended to the lower surface side of the quartz plate 11 and one ends of the conductive paths 203a, 203b are connected. The other ends of the conductive paths 203a, 203b are pulled out from a bottom portion of the casing 201 and are respectively connected to the conductive paths 21a, 21b of the printed-circuit board 2. In the present embodiment, there is a space between the end faces (faces on which the electrodes 13 are formed) of the quartz plate 11 and side walls of the casing 201, so that a solution storage space 204 includes not only a space surrounded by the surface of the quartz plate 11 on which the capture layer 12 is formed and the casing 201 but also a space surrounded by a lower surface (rear surface) of the quartz plate 11 and the casing 201.

Hereinafter, other examples of the quartz resonator will be described. Each of the capture layers 12 of the quartz resonators 10 shown in FIG. 17 to FIG. 20 is formed on the quartz plate 11 with no metal layer interposed therebetween, but, similar to the previous embodiments, it is also possible to structure such that the metal layer is formed on the plate surface of the quartz plate 11 by being separated from the electrodes on the end faces of the quartz plate 11 and the capture layer is laminated on the metal layer. Further, in an example of FIGS. 17(a) and 17(b), there are provided areas in which electrodes 311 are formed on the end faces of the quartz plate 11 in the entire width direction thereof and areas in which electrodes 311 are drawn out from the electrodes 311 and formed on the center portions in the width direction of the end faces, in which the former electrodes mainly vibrate the quartz plate 11 and the latter electrodes are used to be connected to external electrodes.

In an example of FIGS. 18(a) and 18(b), electrodes 321 are provided on one end sides and the other end sides of the end faces of the quartz plate 11 by leaving spaces therebetween, and the respective electrodes 321 are extended to the lower surface of the quartz plate 11. Specifically, in this example, two sets of electrodes mutually opposite in the Z' direction of the quartz plate 11 are formed in the longitudinal direction of the quartz plate 11. In this case, two electrodes formed on the same end face of the respective sets of electrodes are connected to a common conductive path, for instance. In an example shown in FIGS. 19(a) and 19(b), the structure in FIG. 17 is applied to the two electrodes formed on the same end face shown in FIG. 18. Further, the quartz resonator may also be provided with the capture layers 12 on both surfaces of the quartz plate 11, and as an example of this, FIG. 20 show an example in which this is applied to the structure in FIG. 19.

Further, in examples shown in FIG. 21 to FIG. 24, electrodes are provided not only on the end faces of the quartz plate 11 but also on the plate surface (upper surface) along the left edge and the right edge thereof, and further, the electrodes are provided also on the lower surface of the quartz plate 11 along the left edge and the right edge thereof. In a group of these examples, the capture layer 12 is provided on the entire plate surface of the quartz plate 11, which means that the capture layer is provided also on electrodes 341a, 341b (351a, 352a) formed on the plate surface, so that frequency signals in which a frequency signal generated by a vertical field excitation is superimposed on a frequency signal generated by a parallel field excitation, are obtained from conductive paths. Accordingly, it is possible to detect the frequency signals with higher sensitivity. Here, in examples of FIG. 21 and FIG. 22, the size of electrodes on the upper surface of the quartz plate 11 and the size of electrodes on the lower surface of the plate are mutually different, so that pairs of electrodes which provide the vertical field excitation are sort of asymmetric to each other. On the contrary, in examples of FIGS. 23 and 24, the size of electrodes on the upper surface of the quartz plate 11 and the size of electrodes on the lower surface of the plate are the same, so that pairs of electrodes which provide the vertical field excitation are sort of symmetric to each other. Further, FIG. 21 to FIG. 23 show examples in which the capture layer 12 is provided on one surface side of the quartz plate 11, and FIG. 24 show an example in which the capture layers 12 are provided on both surfaces of the quartz plate.

As above, the structure of electrodes that provide not only the parallel field excitation but also the vertical field excitation may also be applied to the embodiments shown in FIG. 2 or FIG. 12, but, since the Q value is lowered when the degree of vertical field excitation is enlarged, it is desirable to set the degree of vertical field excitation to secure a high Q value. As shown in FIG. 25, for instance, it is structured such that on both surfaces of the quartz plate 11, electrodes 361 continuously provided from electrodes 361 formed on the end faces of the quartz plate 11 are formed only on both left and right edge portions and the capture layers 12 are formed on the electrodes 361 on the upper surface side of the quartz plate 11, and on the upper surface side of the quartz plate 11, the metal layer 11a separated from the electrodes 361 on the end face sides is formed and the capture layer 12 is provided on the metal layer 11a.

Next, measurement experiments were conducted using the quartz sensors according to the embodiments of the present invention.

Experimental Method

Three types of quartz resonators in FIG. 18, FIG. 20 and FIG. 23 described in the embodiments were used in the quartz sensors used in the experiments, and equivalent circuit constants (series resistance R, inductance L, capacitance C and Q value) of the quartz sensors were measured in the atmosphere and in PBS (Phosphate buffered saline) as measurement environments.

Measured Results

Measured results are shown in the following tables. Table 1, Table 2 and Table 3 show results when the measurement was performed by using the quartz resonator in FIG. 18, the quartz resonator in FIG. 20, and the quartz resonator in FIG. 23, respectively, in the quartz sensors. Further, a difference in frequencies when the measurement atmosphere changed from the vapor phase to the liquid phase was 131 Hz in the quartz resonator in FIG. 18, 132 Hz in the quartz resonator in FIG. 20, and 64 Hz in the quartz resonator in FIG. 23.

Examination

Although the series resistance (R) is slightly changed in every quartz resonator in FIG. 18, FIG. 20 and FIG. 23, it can be confirmed that the series resistance of the quartz resonator is large enough to be able to ignore the change. Further, when the Q value in the atmosphere and that in the PBS are compared, the values are about the same, so that it can be confirmed that the stability of frequency is high also in the liquid phase, and the sensing target can be detected with high accuracy.

TABLE 1

|  | R (kΩ) | L (H) | C (F) | Q |
|---|---|---|---|---|
| IN ATMOSPHERE | 39.11 | 18.4548 | 0.08380 | 11999 |
| IN PBS | 39.64 | 18.4577 | 0.08379 | 11840 |

TABLE 2

|  | R (kΩ) | L (H) | C (F) | Q |
|---|---|---|---|---|
| IN ATMOSPHERE | 41.35 | 18.4548 | 0.08380 | 11349 |
| IN PBS | 40.94 | 18.4577 | 0.08379 | 11464 |

TABLE 3

|  | R (kΩ) | L (H) | C (F) | Q |
| --- | --- | --- | --- | --- |
| IN ATMOSPHERE | 14.91 | 18.4813 | 0.08486 | 31299 |
| IN PBS | 14.93 | 18.4815 | 0.08487 | 31257 |

What is claimed is:

1. A quartz sensor having a capture layer for capturing a sensing target in sample solution formed on a plate surface of an AT-cut quartz plate thereof and sensing the sensing target based on a change in a natural frequency of the quartz plate caused when the sensing target is captured by the capture layer, said quartz sensor comprising electrodes which are provided on end faces that are mutually opposite in a Z' direction of the quartz plate, and which are for causing a parallel electric field excitation in the quartz plate, wherein an entirety of both faces of the quartz plate are flat.

2. A quartz sensor having a capture layer for capturing a sensing target in sample solution formed on a plate surface of an AT-cut quartz plate thereof and sensing the sensing target based on a change in a natural frequency of the quartz plate caused when the sensing target is captured by the capture layer, said quartz sensor comprising electrodes for vibrating the quartz plate provided on mutually opposite end faces of the quartz plate, wherein a metal layer insulated from said electrodes is formed on the plate surface of the quartz plate, and the capture layer is formed on the metal layer.

3. A quartz sensor having a capture layer for capturing a sensing target in sample solution formed on a plate surface of an AT-cut quartz plate thereof and sensing the sensing target based on a change in a natural frequency of the quartz plate caused when the sensing target is captured by the capture layer, said quartz sensor comprising electrodes for vibrating the quartz plate provided on mutually opposite end faces of the quartz plate, wherein when said electrodes provided on the end faces of the quartz plate are set as first electrodes, there are mutually opposite second electrodes each provided on a part of each of both plate surfaces of the quartz plate, and said first electrodes and the second electrodes are electrically connected to one another.

4. The quartz sensor according to claim 3, wherein said first electrodes and the second electrodes are electrically connected to one another on the quartz plate.

5. A sensing device, comprising: said quartz sensor according to claim 1; an oscillation circuit connected to said quartz sensor; and a measuring section measuring a frequency signal from said oscillation circuit.

6. The quartz sensor according to claim 1, wherein a metal layer is formed on the plate surface of the quartz plate, and the capture layer is formed on the metal layer.

7. The quartz sensor according to claim 1, wherein when said electrodes provided on the end faces of the quartz plate are set as first electrodes, there are mutually opposite second electrodes each provided on a part of each of both plate surfaces of the quartz plate, and said first electrodes and the second electrodes are electrically connected to one another.

8. The quartz sensor according to claim 7, wherein said first electrodes and the second electrodes are electrically connected to one another on the quartz plate.

9. A quartz sensor, comprising:
an AT-cut quartz plate having a first face and a parallel, opposing second face separated by a plate height, the plate having a length spanning an "X" dimension, a width spanning an orthogonal "Z" dimension, said plate height spanning an orthogonal "Y" dimension, said length being greater than said width, said first face spanning said "X" dimension and "Z" dimension and an entirety of said first face being flat, said second face spanning said "X" dimension and "Z" dimension and an entirety of said second face being flat;
a capture layer capturing a sensing target in sample solution formed on said first face and sensing a sensing target at the capture layer based on a change in a natural frequency of the quartz plate caused when the sensing target is captured by the capture layer;
electrodes provided at opposing plate edges that are at mutually opposite positions along said "Z" dimension of the quartz plate, and which are for causing a parallel electric field excitation in the quartz plate.

10. The quartz sensor according to claim 9, wherein a metal layer is formed on first face of the quartz plate, and the capture layer is formed on the metal layer.

11. The quartz sensor according to claim 9, wherein when said electrodes provided at opposing plate edges are set as first electrodes, and further comprising mutually opposite second electrodes provided respectively on said first face and second face of the quartz plate, and wherein said first electrodes and second electrodes are electrically connected to one an other.

12. The quartz sensor according to claim 11, wherein said first electrodes and the second electrodes are electrically connected to one another on the quartz plate.

* * * * *